United States Patent
Doris

(12) 
(10) Patent No.: US 11,434,461 B2
(45) Date of Patent: Sep. 6, 2022

(54) AIRLIFT PERFUSION BIOREACTOR FOR THE CULTURE OF CELLS

(71) Applicant: KECK GRADUATE INSTITUTE OF APPLIED LIFE SCIENCES, Claremont, CA (US)

(72) Inventor: Corinna Eleni Doris, Claremont, CA (US)

(73) Assignee: KECK GRADUATE INSTITUTE OF APPLIED LIFE SCIENCES, Claremont, CA (US)

( * ) Notice: Subject to any disclaimer, the term of this patent is extended or adjusted under 35 U.S.C. 154(b) by 124 days.

(21) Appl. No.: 16/359,995

(22) Filed: Mar. 20, 2019

(65) Prior Publication Data

US 2019/0292509 A1 Sep. 26, 2019

Related U.S. Application Data

(60) Provisional application No. 62/734,202, filed on Sep. 20, 2018, provisional application No. 62/645,753, filed on Mar. 20, 2018.

(51) Int. Cl.
*C12M 1/00* (2006.01)

(52) U.S. Cl.
CPC .................. *C12M 29/08* (2013.01)

(58) Field of Classification Search
None
See application file for complete search history.

(56) References Cited

U.S. PATENT DOCUMENTS

| | | | | |
|---|---|---|---|---|
| 2,190,596 A * | 2/1940 | Dorr | ............................. | 210/738 |
| 3,847,748 A * | 11/1974 | Gibson | .................. | C12M 29/18 |
| | | | | 435/813 |
| 4,048,017 A * | 9/1977 | Roesler | .................. | C12M 27/24 |
| | | | | 435/813 |
| 4,806,484 A * | 2/1989 | Petrossian | .............. | C12M 29/02 |
| | | | | 435/295.3 |
| 5,320,963 A * | 6/1994 | Knaack | .............. | B01D 21/0039 |
| | | | | 210/615 |
| 5,342,781 A * | 8/1994 | Su | .......................... | C12M 27/20 |
| | | | | 210/194 |

(Continued)

FOREIGN PATENT DOCUMENTS

| EP | 0599651 A2 * | 6/1994 | ............ C12M 27/24 |
|---|---|---|---|
| GB | 1383432 | * | 2/1975 |

(Continued)

OTHER PUBLICATIONS

Gluz. "Modified Airlift Reactors: The Helical Flow Promoters". 1996. Chemical Engineering Science. vol. 51, No. 11. pp. 2915-2920. (Year: 1996).*

(Continued)

*Primary Examiner* — Holly Kipouros
*Assistant Examiner* — Nathan G Esperon
(74) *Attorney, Agent, or Firm* — Lewis Roca Rothgerber Christie LLP

(57) ABSTRACT

An airlift bioreactor for perfusion cell culture comprises a single- or multi-tiered riser for working volume scale-up, an internal inclined gravity settler for cell retention, an outlet port for cell-free spent culture medium removal, and an inlet port for fresh medium addition.

20 Claims, 10 Drawing Sheets

(56) References Cited

U.S. PATENT DOCUMENTS

| | | | | |
|---|---|---|---|---|
| 5,476,783 | A | * | 12/1995 | Mutsakis ............... C12M 25/02 |
| | | | | 435/289.1 |
| 5,817,505 | A | * | 10/1998 | Thompson ............. C12M 33/22 |
| | | | | 435/813 |
| 6,174,434 | B1 | * | 1/2001 | Krofta ................ B01D 17/0205 |
| | | | | 210/221.2 |
| 2003/0147791 | A1 | * | 8/2003 | Ding ................... B01F 33/4051 |
| | | | | 422/231 |
| 2012/0211426 | A1 | * | 8/2012 | Santoro ..................... C02F 9/00 |
| | | | | 210/665 |
| 2017/0197158 | A1 | * | 7/2017 | Kompala ................ B04C 5/103 |
| 2018/0072978 | A1 | * | 3/2018 | Satou ........................ C12P 7/06 |

FOREIGN PATENT DOCUMENTS

| | | | | |
|---|---|---|---|---|
| JP | 63084494 | * | 4/1988 | |
| WO | WO-9106627 A1 | * | 5/1991 | ............... C12N 1/02 |
| WO | WO-2017046720 A1 | * | 3/2017 | .......... B01F 3/04517 |
| WO | WO-2017068265 A1 | * | 4/2017 | ............ C12M 27/02 |
| WO | WO-2017115855 A1 | * | 7/2017 | .............. C12P 5/026 |

OTHER PUBLICATIONS

Knaack. "Conical Bioreactor with Internal Lamella Settler for Perfusion Culture of Suspension Cells". 1994. Animal Cell Technology, pp. 230-233. (Year: 1994).*

Definition of the word "tier". https://www.oxfordlearnersdictionaries.com/us/definition/american_english/tier Accessed Sep. 21, 2021. (Year: 2021).*

Definition of the word "tier". https://www.merriam-webster.com/dictionary/tier Accessed Sep. 21, 2021. (Year: 2021).*

Tyo, Michael Alexander. "The Biochemical Dynamics of Monoclonal Antibody Production in High Density Perfused Fermentors". URL: https://dspace.mit.edu/bitstream/handle/1721.1/43916/31000498-MIT.pdf?sequence=0 Massachusetts Institute of Technology. Feb. 1992. (Year: 1992).*

Gluz. "Modified Airlift Reactors: The Helical Flow Promoters". 1996. Chemical Engineering Science. vol. 41, No. 11, pp. 2915-2920. (Year: 1996).*

* cited by examiner

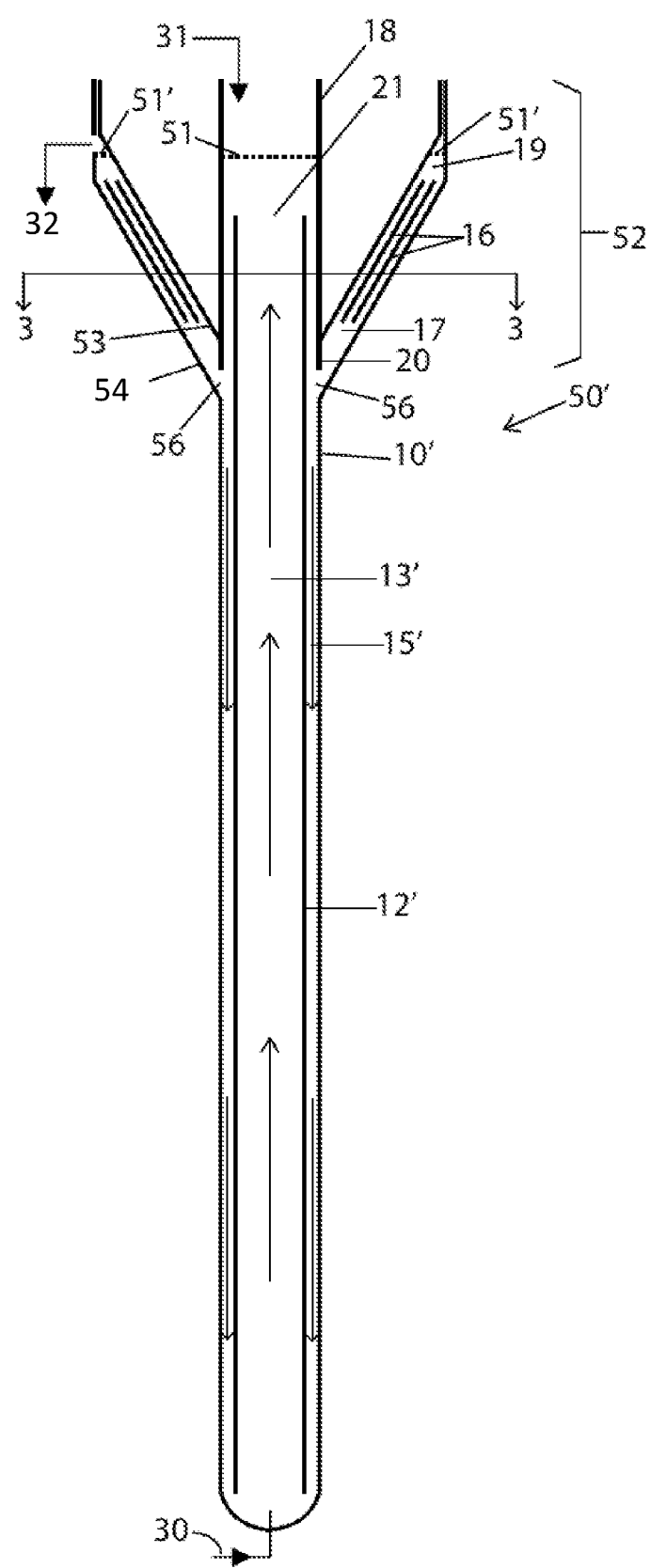

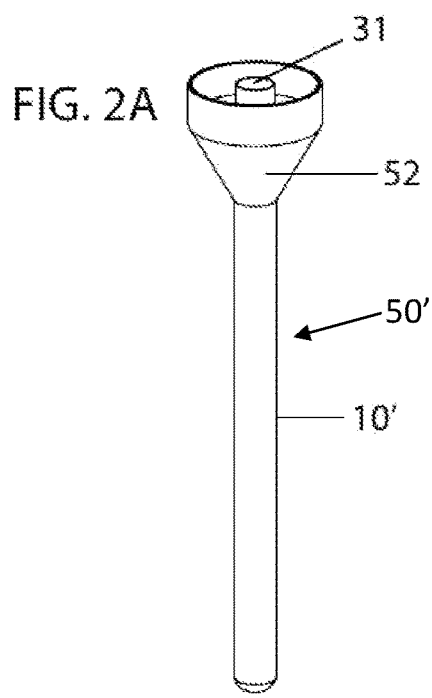
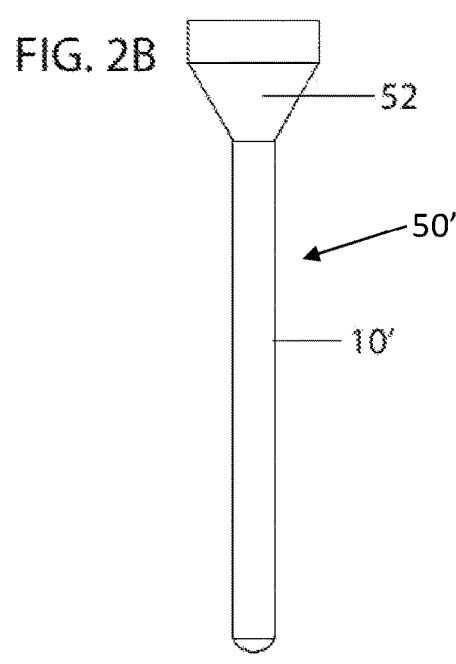
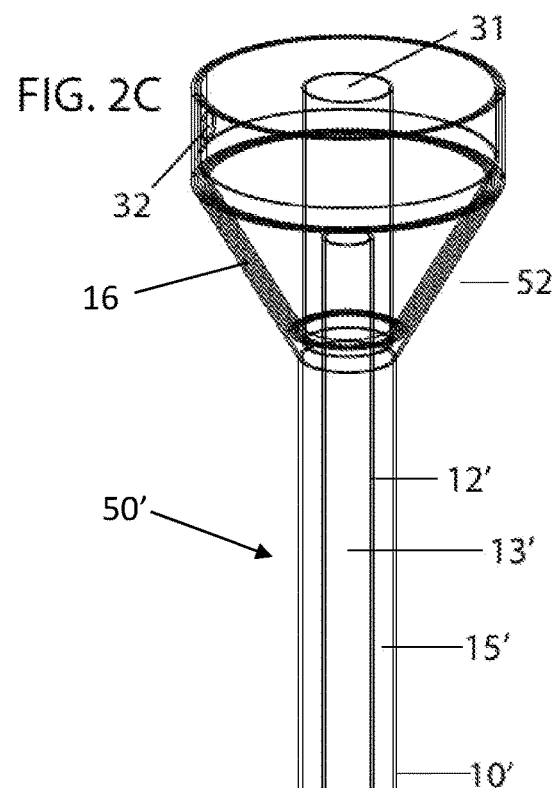

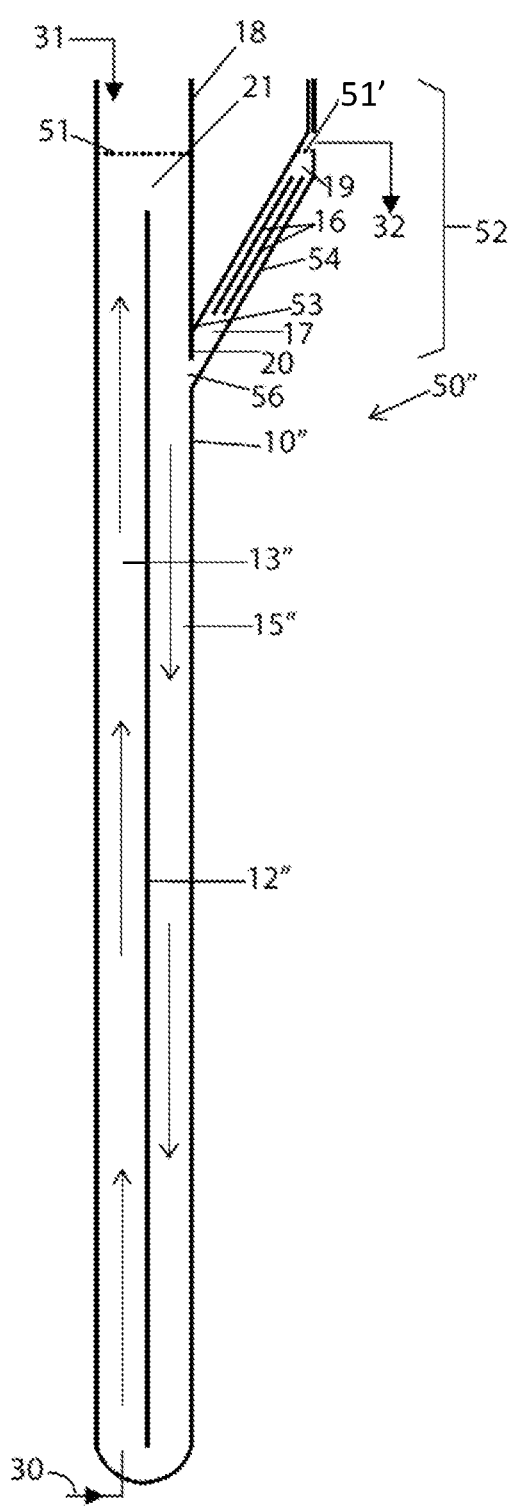

AIRLIFT PERFUSION BIOREACTOR FOR THE CULTURE OF CELLS

CROSS-REFERENCE TO RELATED APPLICATION

This application claims priority to and the benefit of U.S. Provisional Application Nos. 62/645,753 filed Mar. 20, 2018 and 62/734,202 filed Sep. 20, 2018, the entire contents of both of which are incorporated herein by reference.

BACKGROUND

Traditionally, the cell culture process for the production of biotechnology products begins with a seed train volume scale-up where cells are grown and transferred to sequentially larger vessels until sufficient quantity and volume of cells is achieved to inoculate into a larger production bioreactor. The more volume scale-up steps required, the higher the labor requirement and contamination risk.

These processes are also traditionally operated in batch or fed-batch modes of operation. In the batch mode, cells grow and secrete the product of interest into the media until their growth and viability is limited by nutrient depletion and toxic metabolite waste accumulation. In fed-batch mode, higher cell densities are achieved as nutrients are added but waste accumulation still becomes limiting.

The perfusion mode of operation allows for the highest cell densities to be achieved as spent media containing toxic metabolite waste is removed and fresh media containing nutrients is added. The higher cell densities achieved in perfusion mode increase the volumetric productivity and therefore decrease the bioreactor size required. Perfusion culture requires a mechanism for separating the cells from the spent media such that they can be recycled back to the culture. Cell separation techniques most frequently require the removal of the cell-containing culture from the bioreactor, separation of the cells from the spent media in an external separating device, and then return of the cells to the bioreactor. This increases contamination risk and subjects cells to potentially less favorable conditions (e.g. temperature and oxygen levels) external to the bioreactor.

These considerations also apply to the industry's emerging manufacturing of patient-specific cell therapy treatments. Production of these therapies remains a challenge as it requires manufacturing separate batches per patient. The production system must be repeated (scaled-out) as opposed to made larger (scaled-up). This motivates the need for small-scale single patient bioreactors that are capable of expanding cells to therapeutic quantities in processes that can be scaled-out. Process efficiency and scale-out ability can be improved by reducing the complexity, size, and quantity of the cell culture equipment.

Perfusion achieves higher cell density cultures in bioreactors of reduced size; however, external cell separation techniques in addition to the aforementioned weaknesses, are also more challenging to scale-out. The use of multiple vessels per patient batch for the volume scale-up steps is further unfavorable to scale-out efficiency. Additionally, current standard commercial cell culture processes use mechanical agitation to mix the contents of the bioreactor, e.g., shakers, bag rockers, stirred tanks, which adds another component that must be replicated for scale-out.

SUMMARY

According to embodiments of the present disclosure, a bioreactor apparatus includes a cell culture zone comprising a riser section and a downcomer section, a settling zone comprising an inclined gravity settler in fluid communication with the downcomer section and being partitioned from the riser section, a gas injection inlet to the riser section, a liquid inlet to the cell culture zone, and a liquid outlet on the inclined gravity settler. In some embodiments, the bioreactor apparatus may further include a partition between a portion of the inclined gravity settler and a portion of the cell culture zone. The gas injection inlet may include a sparger located at a bottom of the riser section. The bioreactor apparatus may further include a helical flow promoter in a bottom of the downcomer section. In some embodiments, the bioreactor apparatus has a total fluid volume capacity of about 10 mL to about 12,000 L.

In some embodiments, the cell culture zone may include an internal loop airlift reactor, an internal loop concentric tube airlift reactor or an external loop airlift reactor.

According to some embodiments, the cell culture zone may include a multi-tiered draft tube and an external vessel. The riser section may be inside the multi-tiered draft tube, and the downcomer section may be between an outer wall of the multi-tiered draft tube and an inner wall of the external vessel. In some embodiments, the multi-tiered draft tube may further include one or more liquid permeable transition regions between each tier of the multiple-tiered draft tube.

In some embodiments, the cell culture zone may include a generally cylindrical draft tube and an external vessel. The riser section may be inside the generally cylindrical draft tube, and the downcomer section may be between an outer wall of the generally cylindrical draft tube and an inner wall of the external vessel.

According to some embodiments, the cell culture zone may include a tapered draft tube and an external vessel. The riser section may be inside the tapered draft tube, and the downcomer section may be between an outer wall of the tapered draft tube and an inner wall of the external vessel.

In some embodiments, the inclined gravity settler may include a generally hollow interior housing one or more lamella. The one or more lamella may include a plurality of concentric frustoconical lamella or a plurality of parallel rectangular lamella. In some embodiments, the one or more lamella may include a plurality of lamella that is sufficient in number or spacing that the plurality of lamella generally fills a volume between the outer wall of the inclined gravity settler and a partition wall that partitions at least a portion of the inclined gravity settler from at least a portion of the riser section. According to some embodiments, the one or more lamella comprises one or more spiral lamella, or one or more corrugated lamella. The one or more lamella may include a plurality of overlapping lamella or a plurality of staggered lamella.

The one or more lamella may include a plurality of lamella spaced apart from each other horizontally and/or vertically. The plurality of lamella may include a first group of lamella spaced apart from each other horizontally, and a second group of lamella spaced apart from each other horizontally, and the first group of lamella may be spaced apart vertically from the second group of lamella.

BRIEF DESCRIPTION OF THE DRAWINGS

These and other features and advantages of embodiments of the present disclosure may be better understood by reference to the following detailed description considered in conjunction with the drawings, in which:

FIG. 2 is an axial (or side) cross sectional view of a bioreactor apparatus according to embodiments of the present disclosure;

FIG. 2A is a perspective view of the bioreactor apparatus of FIG. 2;

FIG. 2B is a side view of the bioreactor apparatus of FIG. 2;

FIG. 2C is a transparent perspective view of the bioreactor apparatus of FIG. 2 showing the interior of the bioreactor apparatus;

FIG. 3 is an axial (or side) cross sectional view of a bioreactor apparatus according to embodiments of the present disclosure;

DETAILED DESCRIPTION

Embodiments of the present disclosure feature a mechanically simple design with minimal moving parts. Internal separation removes the requirement for a recirculation loop and pump for perfusion mode. Pneumatic agitation removes the requirement for a mechanical agitation method. Integrated and consolidated working volume scale-up and cell separation also minimize manual handling and contamination risk.

According to embodiments of the present disclosure, a bioreactor apparatus provides perfusion cell culture, cell culture volume scale-up, and inclined gravity settler cell separation. In some embodiments, for example, an airlift perfusion bioreactor apparatus has internal working volume scale-up and cell separation capabilities for, e.g., the culture of mammalian cells.

Figure 1:
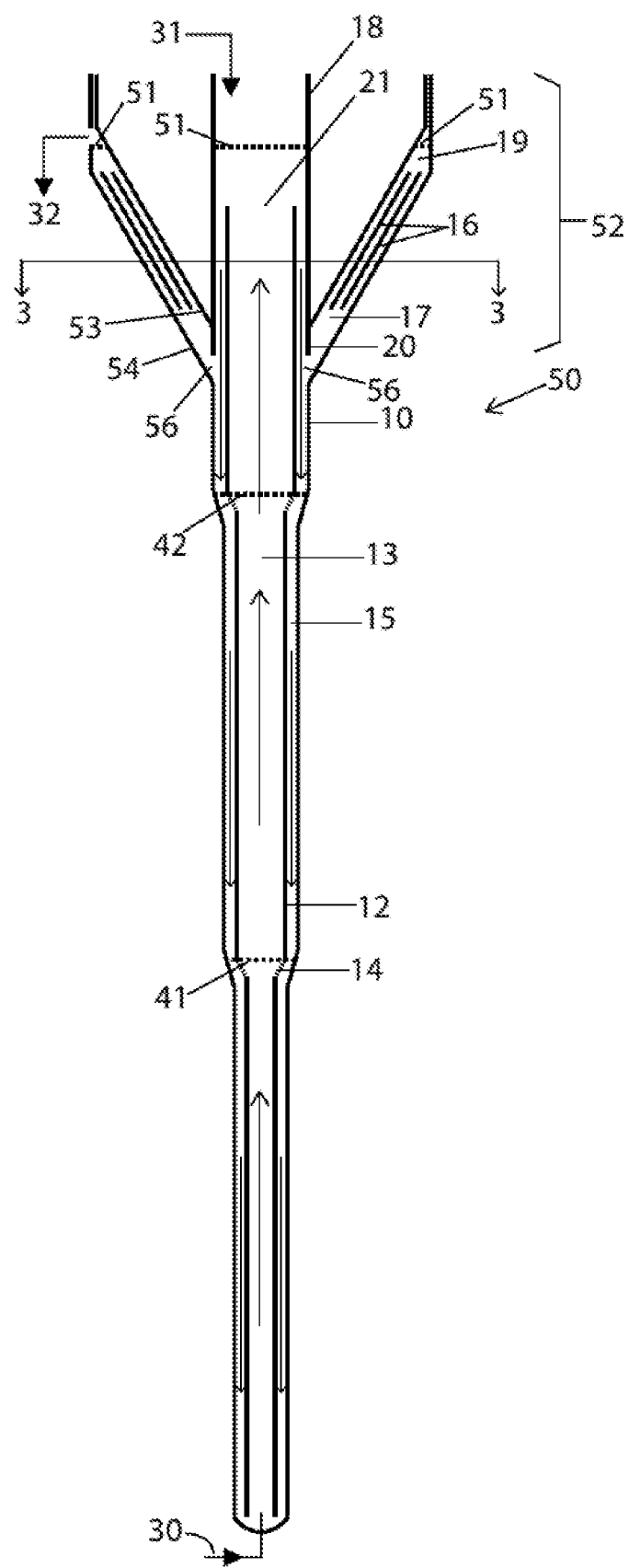
FIG. 1 is an axial (or side) cross sectional view of a bioreactor apparatus according to embodiments of the present disclosure.
Figure 1A:
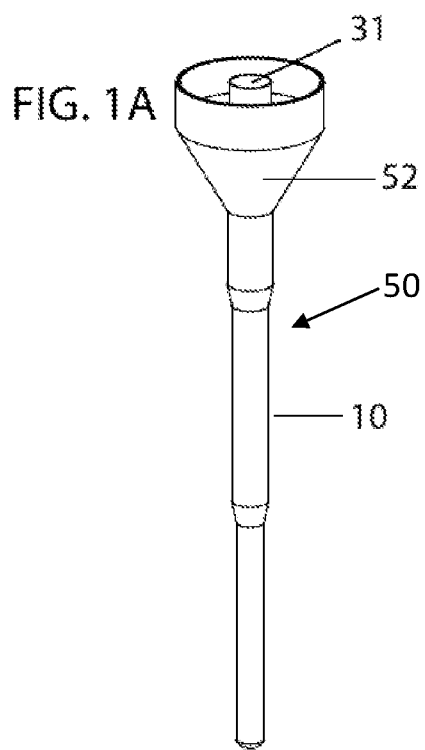
FIG. 1A is a perspective view of the bioreactor apparatus of FIG. 1.
Figure 1B:
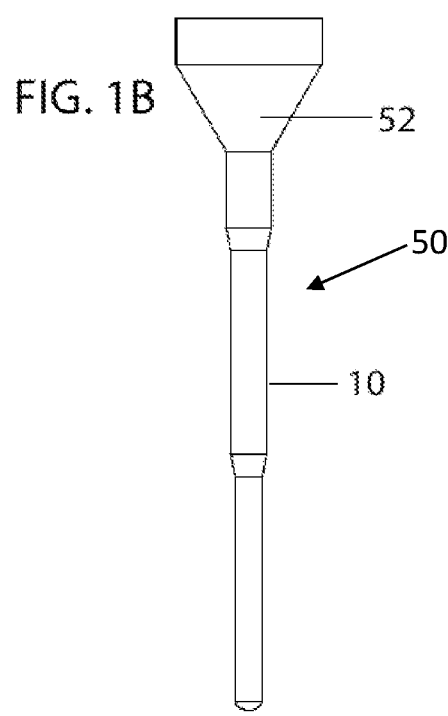
FIG. 1B is a side view of the bioreactor apparatus of FIG. 1.
Figure 1C:
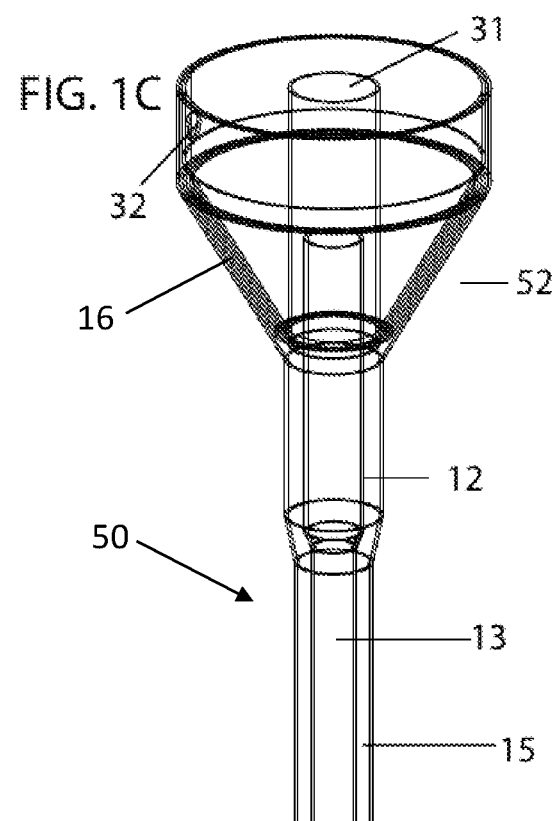
FIG. 1C is a transparent perspective view of the bioreactor apparatus of FIG. 1 showing the interior of the bioreactor apparatus.
Figure 2D:
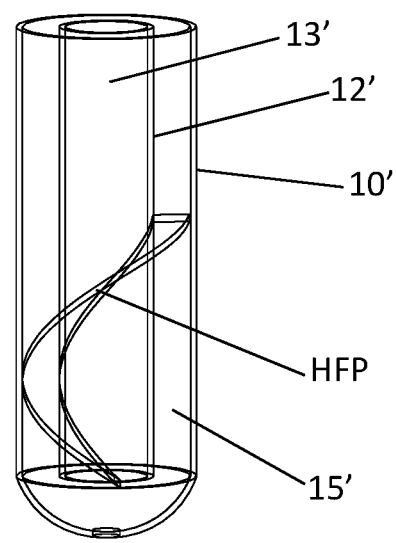
FIG. 2D is a transparent perspective view of an external vessel and draft tube of a bioreactor apparatus having a helical flow promoter according to embodiments of the present disclosure.
Figure 3A:
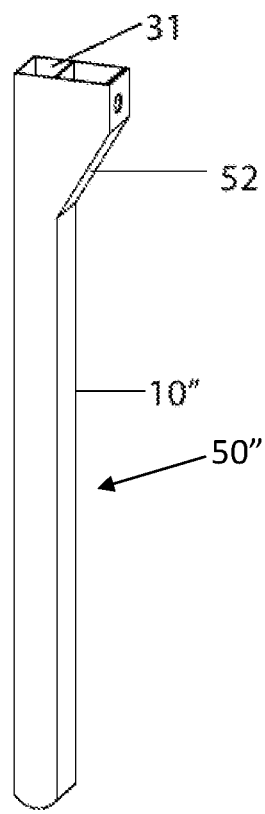
FIG. 3A is a perspective view of the bioreactor apparatus of FIG. 3.
Figure 3B:
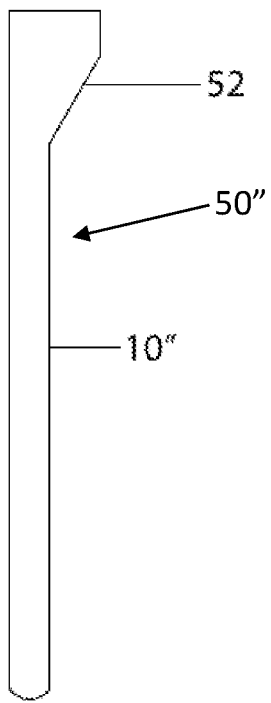
FIG. 3B is a side view of the bioreactor apparatus of FIG. 3.
Figure 3C:
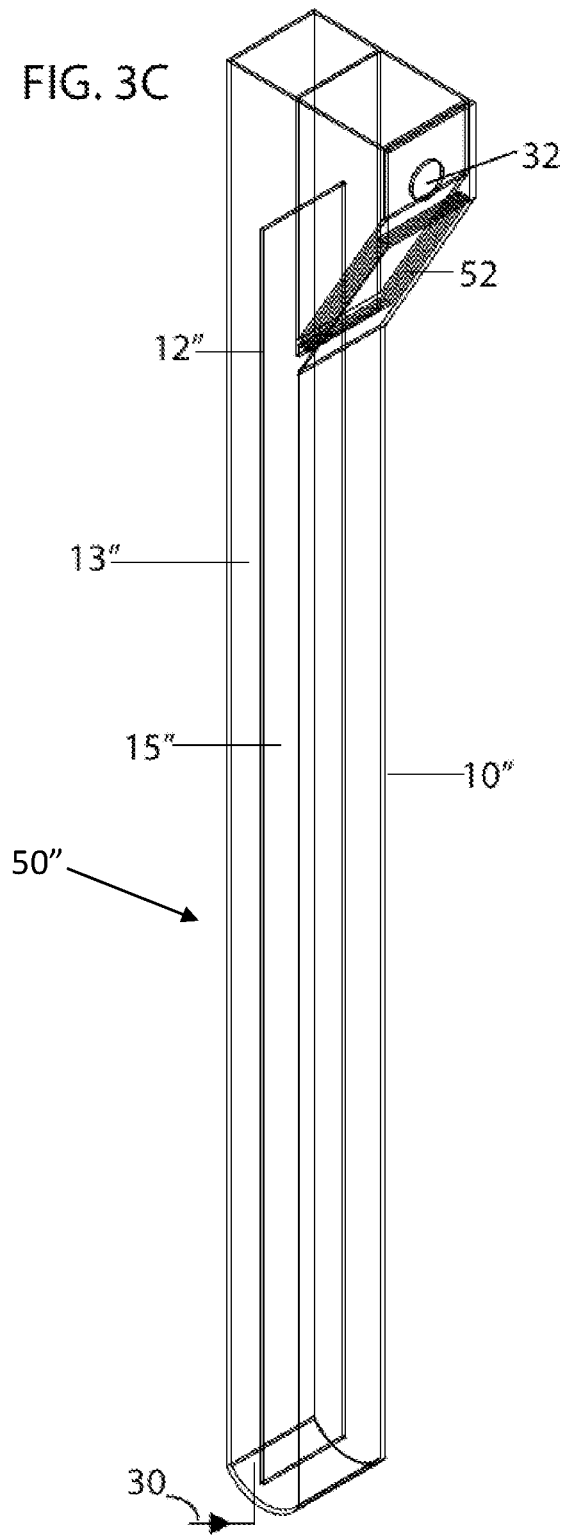
FIG. 3C is a transparent perspective view of the bioreactor apparatus of FIG. 3 showing the interior of the bioreactor apparatus.

For example, in some embodiments, as shown in FIGS. 1 and 1A-C, in FIGS. 2 and 2A-C, and in FIGS. 3 and 3A-C the bioreactor apparatus 50 (or 50' or 50" in FIGS. 2 and 2A-C and in FIGS. 3 and 3A-C) may include an external vessel 10 (or 10' in FIGS. 2 and 2A-2C and 10" in FIGS. 3 and 3A-C) having a settling zone 17, a riser section 13 (riser section 13' in FIGS. 2 and 13" in FIG. 3) and a downcomer section 15 (downcomer section 15' in FIGS. 2 and 15" in FIG. 3). The bioreactor apparatus 50 or 50' or 50" may operate in any suitable manner, and in some embodiments may include an internal-loop airlift bioreactor, an internal—loop concentric tube airlift bioreactor, or an external-loop airlift bioreactor. For example, the bioreactor apparatus 50, 50' or 50" may include a draft tube 12 (or draft tube 12') or riser partition 12" within the external vessel 10, 10', or 10" and the draft tube 12 (or 12') or riser partition 12" and the external vessel 10, 10', or 10" may define a cell culture zone 21 having an inner riser section 13 (riser section 13' in FIGS. 2 and 13" in FIG. 3) inside the draft tube 12 (or 12') or riser partition 12", and an outer downcomer section 15,15', or 15" between the outer wall of the draft tube 12 or 12' or riser partition 12" and the inner wall of the external vessel 10, 10' or 10". The bioreactor apparatus 50, 50' or 50" may be pneumatically driven (e.g., entirely pneumatically driven), e.g., by air (or other oxygen-containing gas) sparged at the bottom of the bioreactor apparatus 50, 50' or 50" via an air (or other oxygen-containing gas) injection inlet 30. In operation, air (or other gas) is sparged through the air injection inlet 30, causing the liquid (e.g., a cell culture) in the apparatus to circulate up through the riser section 13, 13', or 13" (upward arrows in FIGS. 1, 2, and 3) and down through the downcomer section 15, 15', or 15" (downward arrows in FIGS. 1, 2, and 3). In some embodiments, as shown in FIG. 2D, the bioreactor apparatus 50 or 50' may also include a helical flow promoter HFP in the bottom of the downcomer section 15 or 15' in order to generate a helical flow pattern in the downcomer section. This decreases the minimum air flow rate from the air injection inlet to help keep cells suspended in the liquid.

As shown in FIG. 1, the draft tube 12 may include multiple steps or tiers. Such a multi-tiered draft tube 12 enables scaling-up of the cell culture working volume in a stepwise fashion for an internal seed train. In an example three-tier system according to embodiments of the disclosure, the inoculation volume is filled over the first tier of the draft tube 12 to liquid fill level 41 indicated by the horizontal dashed line above the first tier of the draft tube 12. At this volume, the bioreactor apparatus may operate as a smaller airlift. When the cell density is reached where dilution and scale-up to a larger vessel would traditionally occur, here media may be added to over the second tier of the draft tube 12 to liquid fill level 42 indicated by the horizontal dashed line above the second tier of the draft tube 12. Tiers can be added or removed to achieve the desired minimum to maximum working volume ratios. When the media is added to the liquid fill level 51 as indicated by the horizontal dashed line near the top of the partition wall 18 (discussed further below), and the corresponding horizontal dashed lines 51' near the top of the inclined gravity settler 52 (discussed further below), perfusion mode can be initiated.

As can be seen in FIG. 1, the multi-tiered draft tube 12 separates the riser section 13 from the downcomer section 15. In some embodiments, as also shown in FIG. 1, the different tiers of the multi-tiered draft tube 12 are separated by liquid permeable transition regions 14 that allow free liquid flow but also prevent (or minimize) gas phase bubbles from escaping from the riser section 13 into the downcomer section 15. In some embodiments, the transition regions 14 may include cuts or holes in the material of draft tube 12 at the transition regions 14. However, in some embodiments, the transition regions 14 may include spokes, strips, meshes or other suitable patterns of a transition material that connects the tiers at the transition regions 14. The transition material may be any suitable material for effecting an appropriate transition, and may be the same material as the material of the draft tube, or a different material with similar properties to those of the draft tube material.

It is understood that the draft tube 12 is not limited to the multi-tiered construction. Indeed, as shown in FIGS. 2 and 2A-C and described further below, the draft tube 12' may have a generally cylindrical, un-tiered (or single-tiered) structure.

In some embodiments, the settling zone 17 may be defined by an inclined gravity settler 52 near the top of the bioreactor apparatus 50, 50' or 50". As best seen in FIGS. 1C and 2C, the inclined gravity settler 52 may be a generally frustoconical region of the external vessel 10 or 10'. In some embodiments, however, as shown in FIGS. 3 and 3A-3C, the inclined gravity settler 52 may be a generally rectangular region of the external vessel 10 or 10'. The inclined gravity settler 52 may be generally hollow in order to provide a liquid (or fluid) path between the inclined gravity settler 52 and the downcomer section 15, 15', or 15". To provide an internal cell separation and retention mechanism, for example, the generally hollow interior of the inclined gravity settler 52 may include one or more lamella 16. In some embodiments, the lamella 16 may be arranged as concentric frustoconical lamella (e.g., in the frustoconical inclined gravity settler of external vessel 10) or as parallel rectangular lamella (e.g., in the rectangular inclined gravity settler of external vessel 10'). It is understood that although FIGS. 1, 1C, 2, 2C, 3 and 3C depict multiple lamella 16 that are either frustoconical in shape and concentric in arrangement or rectangular in shape and parallel in arrangement, the present disclosure is not limited to such constructions. Indeed, in some embodiments, for example, the inclined gravity settler 52 may include a single lamella 16 which may or may not be frustoconical or rectangular in shape.

Figure 4A:
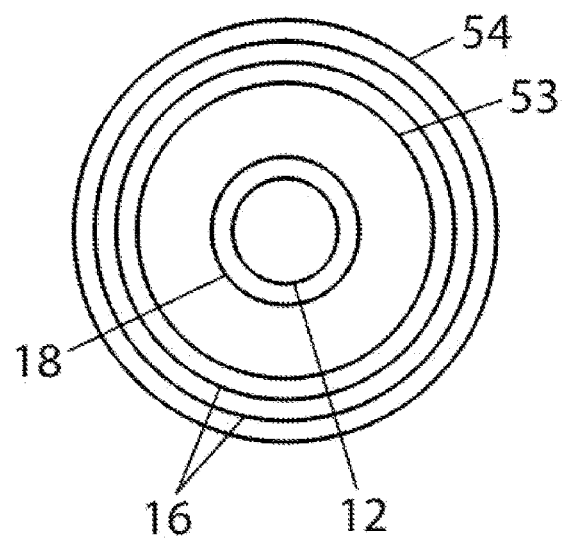
FIG. 4A is a cross-sectional view of a bioreactor apparatus taken along line 3-3 in either FIG. 1 or 2, showing the configuration of the lamella of the inclined gravity settler according to embodiments of the present disclosure.
Figure 5A:
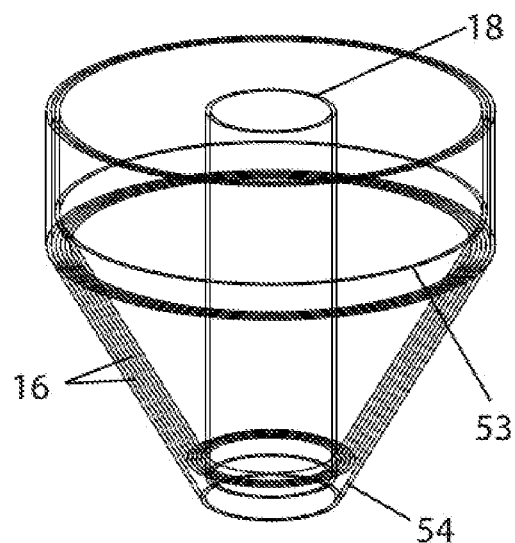
FIG. 5A is a transparent perspective view of the inclined gravity settler and lamella depicted in FIG. 4A.

In embodiments in which the inclined gravity settler 52 includes multiple lamella 16, the lamella 16 may be arranged in any suitable way. For example, as shown in FIGS. 1, 1C, 2, 2C, 4A and 5A, the lamella 16 may generally extend the length of the frustoconical region of the inclined gravity settler 52, and may be arranged concentrically. Also, the lamella 16 may instead have lengths shorter than the length of the frustoconical region of the inclined gravity settler 52, and in some embodiments, the inclined gravity settler may include two or more groups of the concentric lamella 16. When the inclined gravity settler includes two or more groups of concentric lamella 16, the different groups may be separated from each other vertically to create two or more rings of concentric lamella 16 separated along the length of the frustoconical region of the inclined gravity settler 52 as shown in FIG. 5C. However, the lamella may have any suitable size and shape, and may be arranged in any suitable manner so long as the lamella do not hinder or otherwise adversely affect the cell retention function of the inclined gravity settler 52.

Figure 4B:
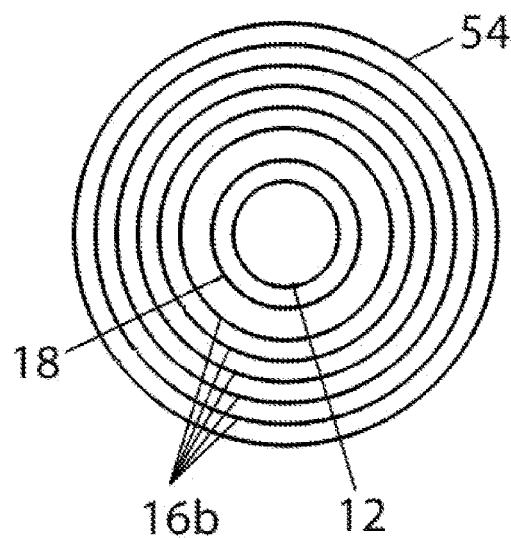
FIG. 4B is a cross-sectional view of a bioreactor apparatus taken along line 3-3 in either FIG. 1 or 2, showing an alternate configuration of the lamella of the inclined gravity settler according to embodiments of the present disclosure.
Figure 5B:
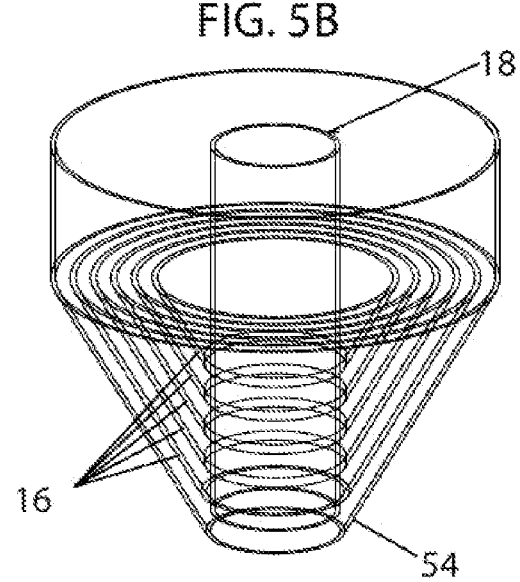
FIG. 5B is a transparent perspective view of the inclined gravity settler and lamella depicted in FIG. 4B.
Figure 5C:
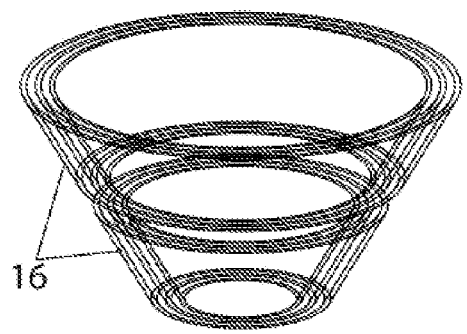
FIG. 5C is a transparent perspective view of the inclined gravity settler showing still another alternate configuration of the lamella according to embodiments of the present disclosure.

For example, in some embodiments, as shown in FIGS. 4B and 5B, the inclined gravity settler 52 may have a significantly larger thickness, and the lamella 16b may be sufficient in number to generally fill the volume between the outer wall 54 of the inclined gravity settler and the partition wall 18. Alternatively, the lamella 16b may include any number of lamella 16b that are spaced apart sufficiently to fill the volume between the outer wall 54 and the partition wall 18. In such configurations, the partition wall 18 also acts as the inner wall 53 of the inclined gravity settler 52. Additionally, as the cross-sectional area defined by the outer wall 54 of the inclined gravity settler 52 and the partition wall 18 is generally triangular in shape, the lamella 16b will have differing lengths in order to fit within the volume between the outer wall 54 and the partition wall 18. For example, as shown in FIG. 5B, while the lamella 16b closer to the outer wall 54 of the inclined gravity settler 52 will be longer, the lamella closer to the partition wall 18 will be shorter in order to provide lamella 16b that are generally concentric in orientation.

Further, each of the concentric lamella 16b may extend either completely around or only partially around the perimeter or circumference of the partition wall 18 or outer wall 54 of the inclined gravity settler 52. When one or more of the concentric lamella 16b extend partially around the perimeter, the concentric lamella 16b may include one or more partial lamella that are separated from each other along the same perimeter horizontally (similar to the configuration of plate-like lamella 16e discussed further below).

Figure 4C:
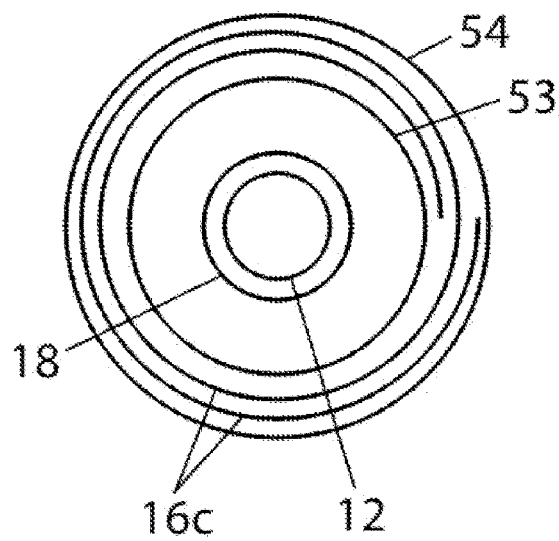
FIG. 4C is a cross-sectional view of a bioreactor apparatus taken along line 3-3 in either FIG. 1 or 2, showing another alternate configuration of the lamella of the inclined gravity settler according to embodiments of the present disclosure.

In other embodiments, as shown in FIG. 4C, the lamella 16c may have a generally spiral shape with a length that generally extends the length of the frustoconical region of the inclined gravity settler 52. In this configuration, as shown in FIG. 4C, the turns of the spiral mimic the concentric lamella 16 depicted in FIGS. 4A and 5A. Also, like the lamella 16 in FIGS. 4A and 5A, the spiral lamella 16c may instead have lengths shorter than the length of the frustoconical region of the inclined gravity settler 52, and in some embodiments, the inclined gravity settler may include two or more groups of the spiral lamella 16c. When the inclined gravity settler includes two or more groups of spiral lamella 16c, the different groups may be separated from each other vertically to create two or more rings of spiral lamella 16c separated along the length of the frustoconical region of the inclined gravity settler 52, as shown generally in FIG. 5C in connection with the concentric lamella 16 configuration. The separation distance between the rings of spiral lamella 16c is not particularly limited, and may be tuned or selected in order to enhance cell retention performance while minimizing impact on fluid flow out of the liquid (or spent media) outlet 32.

Figure 4D:
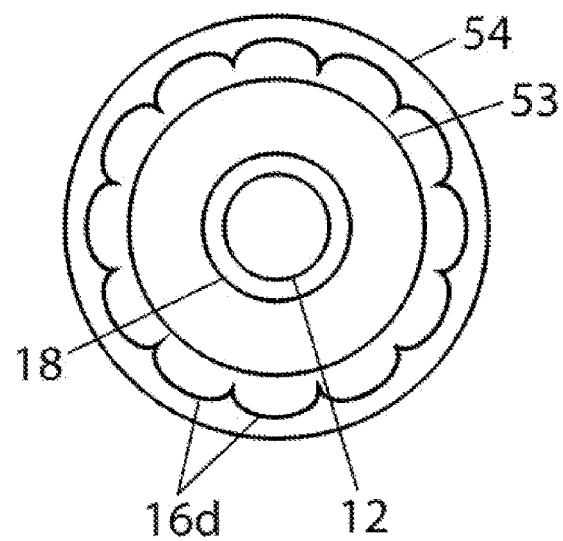
FIG. 4D is a cross-sectional view of a bioreactor apparatus taken along line 3-3 in either FIG. 1 or 2, showing yet another alternate configuration of the lamella of the inclined gravity settler according to embodiments of the present disclosure.

In other embodiments, as shown in FIG. 4D, the lamella 16d may have a generally corrugated shape resembling the folds of a hand fan. In the depicted configuration, the folds or pleats of the lamella 16d are generally rounded, but it is understood that the present disclosure is not limited to this configuration. Indeed, in some embodiments, the pleats or folds of the lamella 16d may be more pointed, thus presenting a generally triangular corrugated pattern, rather than the rounded pattern shown in FIG. 4D. In either configuration, the lamella 16b may also have a length that generally extends the length of the frustoconical region of the inclined gravity settler 52.

Also, like the lamella 16 in FIGS. 4A and 5A, the lamella 16d may also have lengths shorter than the length of the frustoconical region of the inclined gravity settler 52, and the inclined gravity settler 52 may include two or more groups of the corrugated lamella 16d. When the inclined gravity settler includes two or more groups of corrugated lamella 16f, the different groups of lamella may be separated from each other vertically to create two or more rings of overlapping lamella separated along the length of the frustoconical region of the inclined gravity settler 52, as shown in FIG. 5C in connection with the lamella 16 of FIGS. 4A and 5A. The degree to which the lamella 16d are pleated or folded (i.e., the number of pleats or folds, or the dimensions of the pleats or folds) is not particularly limited, and may be tuned or selected in order to enhance cell retention performance while minimizing impact on fluid flow out of the liquid (or spent media) outlet 32.

Additionally, although FIG. 4D depicts a single layer of overlapping lamella 16d, it is understood that any number of concentric such layers can also be used. For example, the inclined gravity settler can include two or more concentric layers of corrugated lamella 16d. Also, the two or more concentric layers of corrugated lamella 16d can extend generally the length of the frustoconical region of the inclined gravity settler 52, or can be shorter than the inclined gravity settler 52, and include two or more groups of concentric corrugated lamella 16d that are separated vertically, as generally discussed above.

Further, in addition to, or instead of being spaced apart vertically, the one or more groups of corrugated lamella 16d may alternatively or additionally be separated from each other horizontally. For example, when spaced horizontally but not vertically, the inclined gravity settler 52 can include two or more groups of corrugated lamella 16d that are spaced from each other horizontally but that each extend generally the length of the frustoconical region of the inclined gravity settler 52. When the lamella 16d are spaced from each other both horizontally and vertically, the inclined gravity settler 52 can include patches of corrugated lamella 16d resembling a "polka dot" pattern (where each "polka dot" is a patch of corrugated lamella 16d).

Figure 4E:
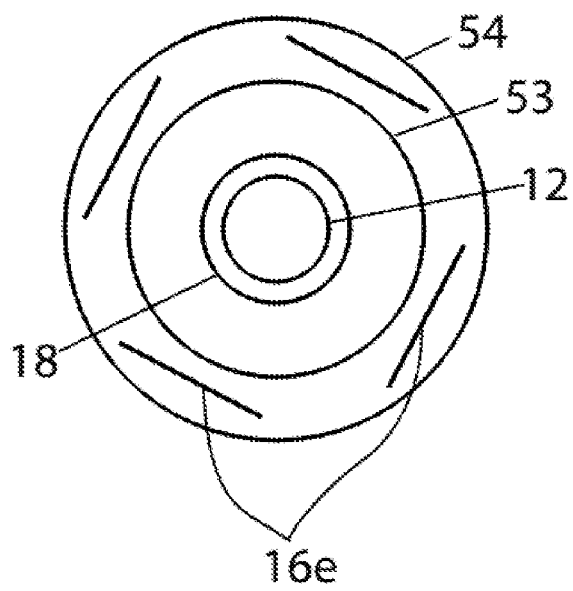
FIG. 4E is a cross-sectional view of a bioreactor apparatus taken along line 3-3 in either FIG. 1 or 2, showing yet another alternate configuration of the lamella of the inclined gravity settler according to embodiments of the present disclosure.

In other embodiments, as shown in FIG. 4E, the lamella 16e may have a generally plate-like shape with a length that generally extends the length of the frustoconical region of the inclined gravity settler. In this configuration, although not shown in FIG. 4E, the plate-like lamella 16e may have a slight curvature in order to conform to the shape of the hollow interior of the gravity settler, but they are otherwise generally square or rectangular (depending on the length of the inclined gravity settler) and are separated from each other by a predetermined or specified distance. The separation distance between the lamella 16e is not particularly limited, and may be tuned or selected in order to enhance cell retention performance while minimizing impact on fluid flow out of the liquid (or spent media) outlet 32.

Also, like the lamella 16 in FIGS. 4A and 5A, the lamella 16e may also have lengths shorter than the length of the frustoconical region of the inclined gravity settler 52, and the inclined gravity settler may include two or more groups of the plate-like lamella 16e. When the inclined gravity settler includes two or more groups of plate-like lamella 16e, the different groups of lamella 16e may be separated from each other vertically to create two or more rings of plate-like lamella 16e separated along the length of the frustoconical region of the inclined gravity settler 52. This configuration would yield a first ring of lamella 16e including lamella that are separated from each other horizontally, and a second ring of lamella 16e separated vertically from the first ring, and also including lamella that are separated from each other horizontally.

Figure 4F:
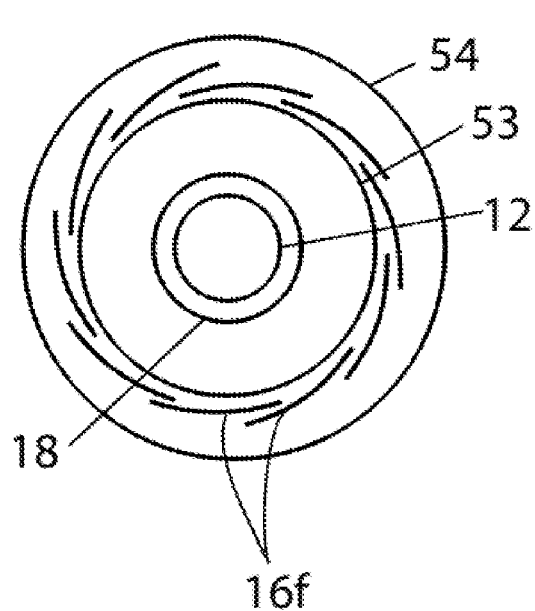
FIG. 4F is a cross-sectional view of a bioreactor apparatus taken along line 3-3 in either FIG. 1 or 2, showing yet another alternate configuration of the lamella of the inclined gravity settler according to embodiments of the present disclosure.

As another example, in some embodiments, as shown in FIG. 4F, the lamella 16f may again have a generally plate-like shape with a length that generally extends the length of the frustoconical region of the inclined gravity settler 52. However, in this configuration, the lamella 16f are arranged in a flower-petal configuration in which the lamella 16f are not concentric or separated from each other by a predetermined distance, but instead overlap one another similar to the petals of a flower (though the lamella do not necessarily contact each other, though they can contact each other in some embodiments). Like the lamella 16e in FIG. 4E, the plate-like lamella 16f in FIG. 4F may also have a slight curvature in order to conform to the shape of the hollow interior of the gravity settler, but are otherwise generally square or rectangular (depending on the length of the inclined gravity settler), though it is understood that these lamella 16f may have any suitable shape and size.

Also, like the lamella 16 in FIGS. 4A and 5A, the lamella 16f may also have lengths shorter than the length of the frustoconical region of the inclined gravity settler 52, and the inclined gravity settler 52 may include two or more groups of the overlapping lamella 16f. When the inclined gravity settler includes two or more groups of overlapping lamella 16f, the different groups of lamella may be separated from each other vertically to create two or more rings of overlapping lamella separated along the length of the frustoconical region of the inclined gravity settler 52, as shown in FIG. 5C in connection with the lamella 16 of FIGS. 4A and 5A. The degree to which the lamella 16f overlap each other is not particularly limited, and may be tuned or selected in order to enhance cell retention performance while minimizing impact on fluid flow out of the liquid (or spent media) outlet 32.

Additionally, although FIG. 4F depicts a single layer of overlapping lamella 16f, it is understood that any number of concentric such layers can also be used. For example, the inclined gravity settler can include two or more concentric layers of overlapping lamella 16f. Also, the two or more concentric layers of overlapping lamella 16f can extend generally the length of the frustoconical region of the inclined gravity settler 52, or can be shorter than the inclined gravity settler 52, and include two or more groups of concentric overlapping lamella 16f that are separated vertically, as generally discussed above.

Further, in addition to, or instead of being spaced apart vertically, the one or more groups of overlapping lamella 16f may alternatively or additionally be separated from each other horizontally. For example, when spaced horizontally but not vertically, the inclined gravity settler 52 can include two or more groups of overlapping lamella 161 that are spaced from each other horizontally but that each extend generally the length of the frustoconical region of the inclined gravity settler 52. When the lamella 16*f* are spaced from each other both horizontally and vertically, the inclined gravity settler 52 can include patches of overlapping lamella 16*f* resembling a "polka dot" pattern (where each "polka dot" is a patch of overlapping lamella 16*f*).

Figure 4G:
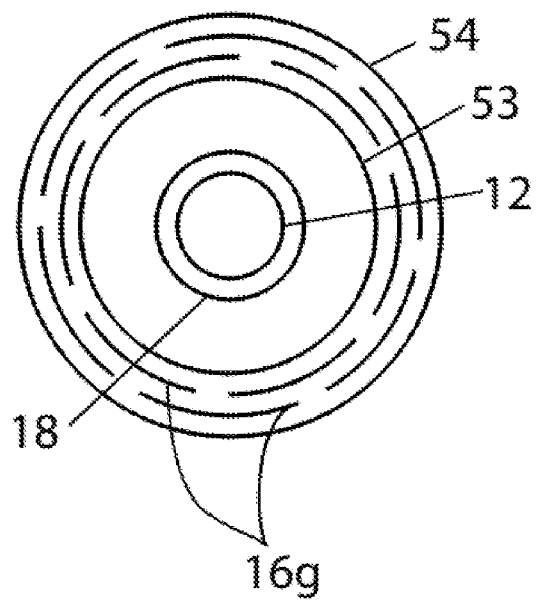
FIG. 4G is a cross-sectional view of a bioreactor apparatus taken along line 3-3 in either FIG. 1 or 2, showing yet another alternate configuration of the lamella of the inclined gravity settler according to embodiments of the present disclosure

In another example, in some embodiments, as shown in FIG. 4G, the lamella 16*g* may again have a generally plate-like shape with a length that generally extends the length of the frustoconical region of the inclined gravity settler 52. However, in this configuration, the lamella 16*g* are arranged in a staggered, multi-layered configuration in which two or more rings of spaced apart lamella 16*g* are arranged generally concentrically, but the rings are offset from each other such that the lamella in a first ring are not aligned with the lamella of a second (adjacent) ring. Like the lamella 16*e* in FIG. 4E and the lamella 16*f* in FIG. 4F, the staggered lamella 16*g* in FIG. 4G may also have a slight curvature in order to conform to the shape of the hollow interior of the gravity settler, but are otherwise generally square or rectangular (depending on the length of the inclined gravity settler), though it is understood that these lamella 16*g* may have any suitable shape and size.

Also, like the lamella 16 in FIGS. 4A and 5A, the lamella 16*g* may also have lengths shorter than the length of the frustoconical region of the inclined gravity settler 52, and the inclined gravity settler 52 may include two or more groups of the staggered lamella 16*g*. When the inclined gravity settler 52 includes two or more groups of staggered lamella 16*g* the different groups of lamella may be separated from each other vertically to create two or more rings of staggered lamella 16*g* separated along the length of the frustoconical region of the inclined gravity settler 52, as shown in FIG. 5C in connection with the lamella 16 of FIGS. 4A and 5A. The degree to which the lamella 16*g* are staggered is not particularly limited, and may be tuned or selected in order to enhance cell retention performance while minimizing impact on fluid flow out of the liquid (or spent media) outlet 32.

Additionally, although FIG. 4G depicts three layers of staggered lamella 16*g*, it is understood that any number of concentric such layers can also be used. For example, the inclined gravity settler 52 can include two or more concentric layers of staggered lamella 16*g*. Also, the two or more concentric layers of overlapping lamella 16*g* can extend generally the length of the frustoconical region of the inclined gravity settler 52, or can be shorter than the inclined gravity settler 52, and include two or more groups of staggered lamella 16*g* that are separated vertically, as generally discussed above.

Further, in addition to, or instead of being spaced apart vertically, the one or more groups of staggered lamella 16*g* may alternatively or additionally be separated from each other horizontally. For example, when spaced horizontally but not vertically, the inclined gravity settler 52 can include two or more groups of staggered lamella 16*g* that are spaced from each other horizontally but that each extend generally the length of the frustoconical region of the inclined gravity settler 52. When the groups of lamella 16*g* are spaced from each other both horizontally and vertically, the inclined gravity settler 52 can include patches of staggered lamella 16*g* resembling a "polka dot" pattern (where each "polka dot" is a patch of staggered lamella 16*g*).

The riser section 13 or 13' and the downcomer section 15 or 15' together define a bulk cell culture zone 21, and the settling zone 17 defined by the inclined gravity settler 52 is separated from the bulk cell culture zone 21 by a partition wall 18. This partition wall 18 may take any suitable shape and construction, and may have any suitable size, width and/or length. For example, it is understood that although FIGS. 1 and 2 may depict the partition wall as generally straight (i.e., defining a generally cylindrical shape), the partition wall 18 need not define a generally cylindrical shape, and can instead define any other suitable shape, e.g., a frustoconical shape which may have similarly angled walls to the frustoconical region of the inclined gravity settler 52, or walls that are angled differently from the inclined gravity settler 52. Additionally, the length of the partition wall 18 is not particularly limited, and may be of any length suitable to separate the settling zone 17 from the bulk cell culture zone 21 without adversely affecting the operation of the bioreactor apparatus 50. For example, in some embodiments, the partition wall 18 may terminate at the inner wall 53 of the inclined gravity settler 52, or may extend somewhat past the inner wall 53 but terminate at point 20 before the outer wall 54 of the inclined gravity settler 52. In embodiments in which the partition wall 18 terminates at a point 20 between the inner wall 53 and outer wall 54 of the inclined gravity settler 52, momentum and upward velocity in the settling zone 17 can be minimized.

In operation (e.g., perfusion), liquid (e.g., a cell culture, or culture media) is added to the bulk cell culture zone 21 via the liquid inlet 31 at the top of the bioreactor apparatus 50 or 50'. The liquid fill level 51 is indicated by the horizontal dashed line near the top of the partition wall 18, and the corresponding horizontal dashed lines 51' near the top of the inclined gravity settler 52. However, it is understood that the liquid fill line is not particularly limited, and liquid may be added to the bioreactor apparatus in any suitable amount to any suitable fill line so long as it will not adversely affect operation of the bioreactor apparatus 50 or 50'. In operation, as media (or liquid) is added to the bulk cell culture zone 21, spent media (or liquid) near the top 19 of the settling zone 17 overflows and exits the bioreactor apparatus 50 or 50' through a spent media outlet 32 near the top of the inclined gravity settler 52. In more detail, the media (or liquid) added through the liquid inlet 31 fills the bulk cell culture zone 21 (including the draft tube 12 (i.e., the riser section 13 or 13'), the downcomer section 15 or 15' and the generally hollow interior of the inclined gravity settler 52 (as shown by the dashed liquid fill lines 51 and 51' in FIGS. 1 and 2).

To operate (e.g., perfusion operation) the bioreactor apparatus 50 or 50', the media (or liquid) is continuously added to the bioreactor apparatus 50 or 50' through the liquid inlet 31, and air (or other gas, e.g., oxygen-containing gas) is sparged into the bioreactor apparatus 50 or 50' through the air injection inlet 30 at the bottom of the bioreactor apparatus 50 or 50'. The media may be continuously added through the liquid inlet 31 at any suitable flow rate so long as the flow rate allows sufficient time for the cells in the media to settle and be retained. As would be understood by those of ordinary skill in the art, the flow rate necessary to accomplish these goals may vary depending on the specific reactor dimensions and the size of the cells being retained, and those ordinary artisans would be capable of determining the requisite flow rate by no more than routine calibration or experimentation.

The introduction of air (or other gas) through the air injection inlet 30 into the riser section 13 or 13' creates a pressure difference between the riser section 13 or 13' and the downcomer section 15 or 15'. This pressure difference drives the liquid in the riser section 13 or 13' to rise or travel upward back towards the top of the bioreactor apparatus 50 or 50'. At the same time, the pressure difference causes the liquid in the downcomer section 15 or 15' to fall or travel downward towards the bottom of the bioreactor apparatus 50 or 50'. Meanwhile, the cells in the culture media are retained in the bioreactor apparatus 50 or 50' by virtue of the settling zone 17. Specifically, as seen best in FIGS. 1 and 2, entrance to the generally hollow interior of the inclined gravity settler 52 is restricted by the relatively small opening 56 into that region from the downcomer section 15 or 15'. Additionally, the relatively narrow interior of the inclined gravity settler 52 as well as the one or more lamella 16 in that component further restrict the momentum and upward velocity of the media and any cells within the media entering that region. As such, the construction of the settling zone 17 and the inclined gravity settler 52 maximizes cell retention within the bioreactor apparatus 50 or 50' while allowing for the efficient and effective removal of spent media.

As discussed generally above, FIGS. 2 and 2A-C depict embodiments of the bioreactor apparatus 50' in which the draft tube 12' and external vessel 10' have a generally cylindrical, un-tiered (or single-tiered) structure. As can be seen in FIGS. 2 and 2A-2C, in some embodiments, the draft tube 12' and the portion of the external vessel 10' housing the draft tube 12' each have a generally uniform diameter providing a generally straight cylindrical structure, though the external vessel 10' has a diameter larger than that of the draft tube in order to provide the riser section 13' and downcomer section 15'. It is understood, however, that the draft tube 12' and external vessel 10' are not limited to such a construction. Indeed, in some embodiments, the draft tube 12' and the portion of the external vessel 10' housing the draft tube 12' may have a tapered construction in which the diameter of each of the draft tube 12' and the external vessel 10' increases from top to bottom at a suitable taper angle, or decreases from top to bottom at a suitable taper angle. Any suitable taper angle may be used in these embodiments. As those of ordinary skill in the art would understand that the taper angle will affect the fluid flow rate through the bioreactor apparatus 50', those ordinary artisans would be capable of determining an appropriate taper angle based on the desired flow rate and/or the size of the cells in the culture media.

Each of the components of the bioreactor apparatuses 50 and 50' described herein can be made of any suitable sterile material that will not leach toxins in the presence of culture media and/or cells or intracellular molecules that may be released into the culture media. Non-limiting examples of suitable materials include stainless steel, glass, or single-use plastics.

Additionally, the bioreactor apparatuses 50 and 50' described herein can have any suitable liquid volume capacity, which may be dictated by various factors, e.g., number of cells or quantity of product desired, etc. However, in some exemplary embodiments, the total liquid or fluid capacity of the bioreactor apparatus may be about 10 mL to about 12,000 L, for example, about 10 mL to about 5 L.

Also, each of the components of the bioreactor apparatuses 50 and 50' described herein can have any suitable dimensions (e.g., length, width, angle of incline in the inclined gravity settler, etc.), as well as any suitable ratio of one dimension to another. Indeed, those of ordinary skill in the art would recognize that these dimensions and ratios will dictate the liquid volume capacity, flow rate, etc. of the bioreactor apparatus. As such, those or ordinary skill in the art would be capable of tuning or selecting the dimensions and dimension ratios to suit the intended use of the bioreactor apparatus.

Although various embodiments of the disclosure have been described, additional modifications and variations will be apparent to those skilled in the art. For example, the components of the bioreactor apparatus may have differing shapes or dimensions, and may be generally tailored to suit the particular culture media and cells intended for use with the apparatus. Indeed, the various shapes, sizes, angles and dimensions of the components of the bioreactor apparatuses described herein by way of example embodiments may be modified in accordance with the knowledge in the field to which the various embodiments pertain. As such, the disclosure is not limited to the embodiments specifically disclosed, and the embodiments may be modified without departing from the disclosure, which is limited only by the appended claims and equivalents thereof.

Throughout the text and claims, any use of the word "about" and like terms reflects the penumbra of variation associated with measurement, significant figures, and interchangeability, all as understood by a person having ordinary skill in the art to which this disclosure pertains. Further, as used herein, the term "generally" and like terms are used as terms of approximation and not as a term of degree, and are intended to account for normal variations and deviations in the measurement, observation or assessment associated with the various components.

What is claimed is:

1. A bioreactor apparatus, comprising:
    a cell culture zone comprising a riser section and a downcomer section, wherein the cell culture zone comprises a multi-tiered draft tube and a correspondingly multi-tiered external vessel, the riser section being inside the multi-tiered draft tube, and the downcomer section being between an outer surface of the multi-tiered draft tube and an inner surface of the correspondingly multi-tiered external vessel, the inner surface of the correspondingly multitiered external vessel being coextensive with an outer surface of the correspondingly multitiered external vessel,
    the multi-tiered draft tube comprising:
        a first draft tube tier having a first draft tube tier diameter, and
        a second draft tube tier having a second draft tube tier diameter, the second draft tube tier diameter being different from the first draft tube tier diameter, and
    the correspondingly multi-tiered external vessel comprising:
        a first external vessel tier corresponding in position to the first draft tube tier of the multi-tiered draft tube such that the first draft tube tier and the first external vessel tier are generally concentric, the first external vessel tier having a first external vessel tier diameter that is greater than the first draft tube tier diameter, and
        a second external vessel tier corresponding in position to the second draft tube tier of the multi-tiered draft tube such that the second draft tube tier and the second external vessel tier are generally concentric, the second external vessel tier having a second external vessel tier diameter that is different from the first external vessel tier diameter and greater than the second draft tube tier diameter;
    the cell culture zone further comprising a first liquid permeable transition region between the first draft tube tier and the second draft tube tier, the first liquid permeable transition region being configured to permit liquid to permeate through the first liquid permeable transition region but to minimize permeation of gas through the first liquid permeable transition region;

a settling zone comprising an inclined gravity settler in fluid communication with the downcomer section, the inclined gravity settler being partitioned from the riser section;

a gas injection inlet to the riser section;

a liquid inlet to the cell culture zone; and a liquid outlet on the inclined gravity settler.

2. The bioreactor apparatus according to claim 1, wherein the inclined gravity settler comprises a generally hollow interior between the outer wall and the inner wall of the inclined gravity settler, the generally hollow interior housing one or more lamella.

3. The bioreactor apparatus according to claim 2, wherein the one or more lamella comprises a plurality of concentric frustoconical lamella or a plurality of parallel rectangular lamella.

4. The bioreactor apparatus according to claim 2, wherein the one or more lamella comprises a plurality of lamella that is sufficient in number or spacing such that the plurality of lamella generally fills a volume of the generally hollow interior.

5. The bioreactor apparatus according to claim 2, wherein the one or more lamella comprise one or more spiral lamella.

6. The bioreactor apparatus according to claim 2, wherein the one or more lamella comprises one or more corrugated lamella.

7. The bioreactor apparatus according to claim 2, wherein the one or more lamella comprises a plurality of overlapping lamella or a plurality of staggered lamella.

8. The bioreactor apparatus according to claim 2, wherein the one or more lamella comprises a plurality of lamella spaced apart from each other horizontally and/or vertically.

9. The bioreactor apparatus according to claim 8, wherein the plurality of lamella comprises a first group of lamella spaced apart from each other horizontally, and a second group of lamella spaced apart from each other horizontally, the first group of lamella being spaced apart vertically from the second group of lamella.

10. The bioreactor apparatus according to claim 1, wherein the bioreactor apparatus has a total fluid volume capacity of about 10 mL to about 12,000 L.

11. The bioreactor apparatus according to claim 1, wherein the gas injection inlet comprises a sparger located at a bottom of the riser section.

12. The bioreactor apparatus according to claim 1, further comprising a helical flow promoter in a bottom of the downcomer section.

13. The bioreactor apparatus according to claim 1, wherein the multi-tiered draft tube comprises a unitary construction, and the first liquid permeable transition region comprises one or more holes in a material of the multi-tiered draft tube between the first and second draft tube tiers.

14. The bioreactor apparatus according to claim 1, wherein the first liquid permeable transition region comprises a patterned transition material between the first and second draft tube tiers.

15. The bioreactor apparatus according to claim 14, wherein the patterned transition material comprises a transition material having a spoke, strip or mesh pattern.

16. The bioreactor apparatus according to claim 1, wherein:

the multi-tiered draft tube further comprises a third draft tube tier having a third draft tube tier diameter, the third draft tube tier diameter being different from both the first and second draft tube tier diameters, and the correspondingly multi-tiered external vessel comprises a third external vessel tier corresponding in position to the third draft tube tier of the multi-tiered draft tube such that the third draft tube tier and the third external vessel tier are generally concentric, the third external vessel tier having a third external vessel tier diameter that is different from both the first and second external vessel tier diameters and greater than the third draft tube tier diameter; and the cell culture zone further comprises a second liquid permeable transition region between the second draft tube tier and the third draft tube tier, the second liquid permeable transition region being configured to permit liquid to permeate through the second liquid permeable transition region but to minimize permeation of gas through the second liquid permeable transition region.

17. The bioreactor apparatus according to claim 1, wherein:

the multi-tiered draft tube further comprises one or more additional draft tube tiers, each having a corresponding draft tube tier diameter, the corresponding draft tube tier diameter of each of the one or more additional draft tube tiers being different from each other and different from both the first and second draft tube tier diameters, and the correspondingly multi-tiered external vessel comprises one or more additional external vessel tiers corresponding in number and position to the one or more additional draft tube tiers of the multi-tiered draft tube such that corresponding ones of the one or more additional external vessel tiers and the one or more additional draft tube tiers are generally concentric, each of the one or more additional external vessel tiers having a corresponding external vessel tier diameter, the corresponding external vessel tier diameter of each of the one or more additional external vessel tiers being different from each other, different from both the first and second external vessel tier diameters, and greater than the corresponding draft tube tier diameter of the corresponding one or more additional draft tube tiers; and the cell culture zone further comprises one or more additional liquid permeable transition regions between the one or more additional draft tube tiers, the one or more additional liquid permeable transition regions being configured to permit liquid to permeate through the one or more liquid permeable transition regions but to minimize permeation of gas through the one or more liquid permeable transition regions.

18. The bioreactor apparatus according to claim 17, wherein the multi-tiered draft tube comprises a unitary construction, and the one or more additional liquid permeable transition regions comprise one or more holes in a material of the multi-tiered draft tube between the one or more additional draft tube tiers.

19. The bioreactor apparatus according to claim 17, wherein the one or more additional liquid permeable transition regions comprises a patterned transition material between the one or more additional draft tube tiers.

20. The bioreactor apparatus according to claim 19, wherein the patterned transition material comprises a transition material having a spoke, strip or mesh pattern.

* * * * *